(12) United States Patent
Abe

(10) Patent No.: US 8,350,901 B2
(45) Date of Patent: Jan. 8, 2013

(54) ELECTRONIC ENDOSCOPIC APPARATUS

(75) Inventor: Kazunori Abe, Saitama (JP)

(73) Assignee: Fujinon Corporation, Saitama-Shi (JP)

( * ) Notice: Subject to any disclaimer, the term of this patent is extended or adjusted under 35 U.S.C. 154(b) by 1582 days.

(21) Appl. No.: 11/528,415

(22) Filed: Sep. 28, 2006

(65) Prior Publication Data
US 2007/0076975 A1    Apr. 5, 2007

(30) Foreign Application Priority Data
Sep. 30, 2005   (JP) .................................. 2005-289147

(51) Int. Cl.
*H04N 1/04* (2006.01)
(52) U.S. Cl. ......................................................... 348/65
(58) Field of Classification Search .................... 348/45, 348/72, 77, 65; A61B 1/04
See application file for complete search history.

(56) References Cited

U.S. PATENT DOCUMENTS

| | | | | |
|---|---|---|---|---|
| 5,995,111 A | * | 11/1999 | Morioka et al. | 345/592 |
| 6,473,116 B1 | * | 10/2002 | Takahashi | 348/65 |
| 6,545,703 B1 | | 4/2003 | Takahashi et al. | |
| 7,245,325 B2 | * | 7/2007 | Yamaguchi | 348/364 |
| 7,400,354 B2 | * | 7/2008 | Kawanishi | 348/362 |

FOREIGN PATENT DOCUMENTS
JP   2003-250761 A   9/2003

* cited by examiner

*Primary Examiner* — David Czekaj
*Assistant Examiner* — Tracy Li
(74) *Attorney, Agent, or Firm* — Birch, Stewart, Kolasch & Birch, LLP

(57) ABSTRACT

A brightness image is produced from a frame image input from a scope and a high brightness pixel group including pixels next to one another, of which the brightness values exceed a predetermined value, and of which the number exceeds a predetermined value, is detected. Only when the pixel group is detected, a microcomputer performs light amount adjustment. When no high brightness pixel group is detected any more, a brightness blurred image is produced from the brightness image. If the value of a pixel forming the brightness blurred image is greater than or equal to a predetermined value, the value is replaced with zero. If the value is less than or equal to a predetermined value, the value is replaced with a greater value as the value is smaller. Then, brightness conversion is performed on the brightness image by adding the brightness blurred image after replacement to the brightness image.

3 Claims, 5 Drawing Sheets

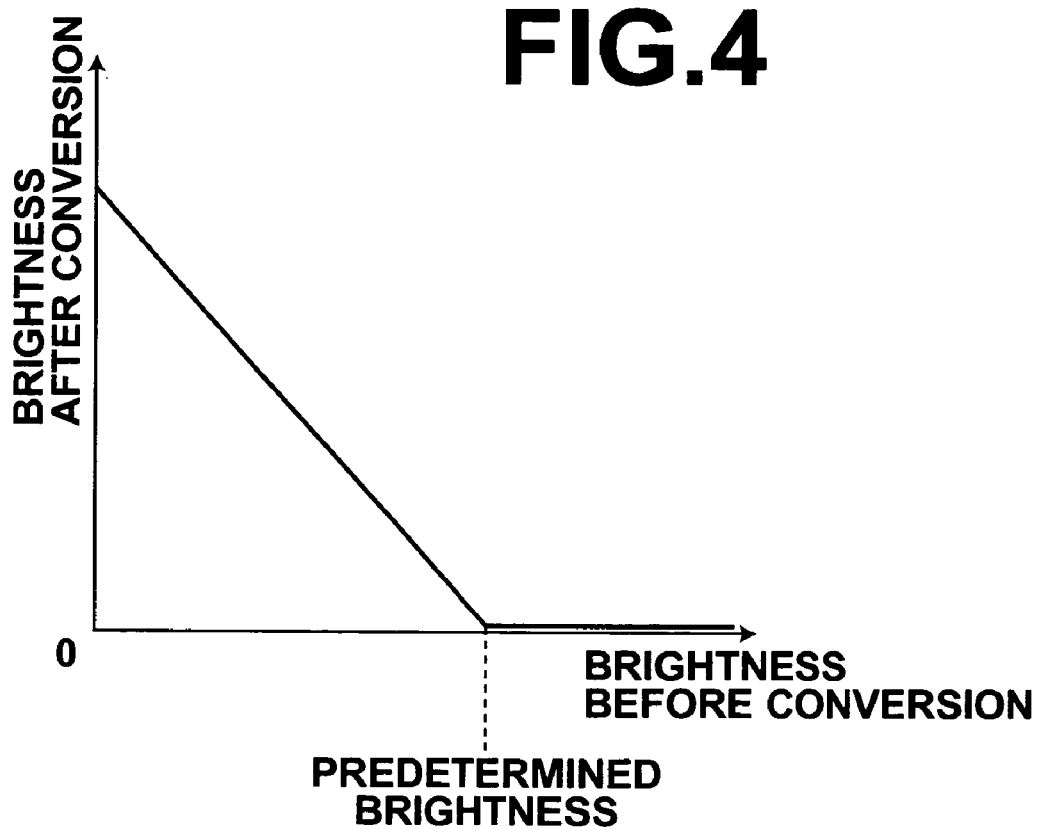

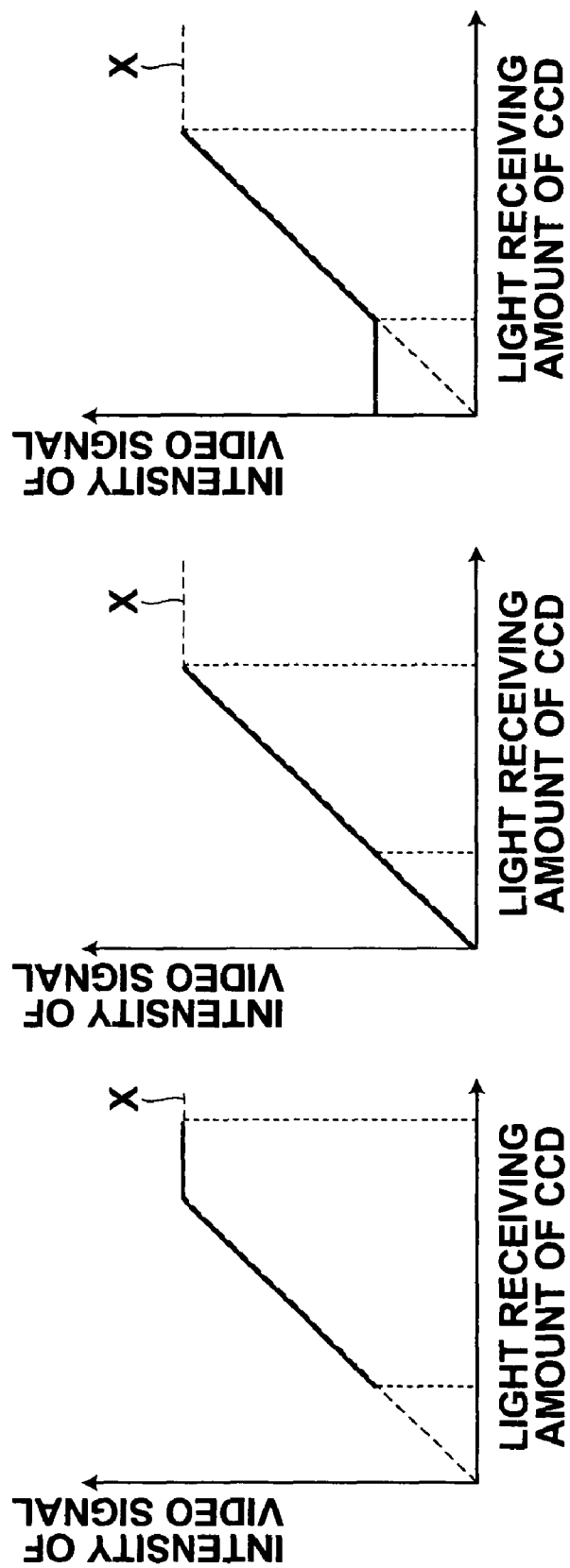

ELECTRONIC ENDOSCOPIC APPARATUS

BACKGROUND OF THE INVENTION

1. Field of the Invention

The present invention relates to an electronic endoscopic apparatus. Particularly, the present invention relates to image processing performed on an image obtained by endoscopic photography.

2. Description of the Related Art

An electronic endoscope obtains an image of an object to be observed (for example, stomach wall) by illuminating the object to be observed with illumination light emitted from the leading edge of the electronic endoscope and by receiving reflection light from the object to be observed at an imaging device (for example, CCD (charge coupled device)) that is mounted on the leading edge of the electronic endoscope. Since endoscopic photography is performed in an enclosed dark space, it is necessary that the illumination light is sufficiently light to obtain an image appropriate for diagnosis. However, if the illumination light is too light, the intensity of reflection light from the object to be observed or a tool (for example, forceps) becomes high, thereby a part of the image becoming white. Consequently, an image of the object to be observed corresponding to the white portion is not obtained (so-called halation).

Methods for suppressing halation have been proposed to solve the aforementioned problem (for example, Japanese Unexamined Patent Publication No. 2003-250761 and U.S. Pat. No. 6,545,703). In these methods, halation is suppressed by detecting the halation based on an average brightness value calculated from the pixel value of each pixel of an imaging device or a density histogram and by reducing the light amount of illumination light by adjusting the aperture diaphragm (iris) of lighting (illumination light).

In these methods, it is possible to surely suppress halation. However, when it is necessary to significantly reduce the light amount to suppress the halation, an obtained image becomes too dark and unclear. Therefore, an image appropriate for diagnosis is not always obtained by using these methods.

Meanwhile, even if halation is present in an image, the image is appropriate for diagnosis in some cases. For example, even if a spot-shaped halation is generated only at one point of the image due to some reasons (such as mirror reflection by a drop of water), if the lightness of the image in the area other than the point is appropriate, the image is recognized as an image appropriate for diagnosis. In other words, elimination of halation and obtainment of an image appropriate for diagnosis are not always identical with each other.

SUMMARY OF THE INVENTION

It is an object of the present invention to solve the problem of halation in endoscopic photography. However, it is not the object of the present invention to completely eliminate the halation. It is the object of the present invention to obtain an image that is truly appropriate for diagnosis by an electronic endoscopic apparatus.

An electronic endoscopic apparatus of the present invention is an electronic endoscopic apparatus comprising:

an endoscope; and a processor for processing an image obtained by the electronic endoscope, wherein the processor includes a light source, an illumination light amount control means, a brightness image production means, a high brightness pixel group detection means and a light amount adjustment means, and wherein the illumination light amount control means controls the light amount of illumination light, which is emitted from the light source and guided to a leading edge of the endoscope, and wherein the brightness image production means produces a brightness image representing the brightness distribution of the image, and wherein the high brightness pixel group detection means detects a high brightness pixel group in the brightness image, and wherein the high brightness pixel group is a group of pixels next to one another, of which the brightness values exceed a predetermined value, and of which the number is greater than or equal to a predetermined number, and wherein when the high brightness pixel group detection means detects a high brightness pixel group, the light amount adjustment means instructs the illumination light amount control means to reduce the light amount until the high brightness pixel group detection means does not detect any high brightness pixel group.

The processor also includes a conversion means for converting the brightness of the image so that the brightness value of a pixel that forms the brightness image, and of which the brightness value is less than or equal to a predetermined value, becomes greater than or equal to the predetermined value. The conversion means converts the brightness of the image by producing a brightness blurred image representing a low frequency component of the brightness image, replacing the brightness value of a pixel that forms the brightness blurred image, and of which the brightness value exceeds a predetermined value, with a zero value, and adding the brightness blurred image after the replacement processing to the brightness image, for example. In this case, it is preferable that the conversion means replaces the brightness value of a pixel that forms the brightness blurred image, and of which the brightness value exceeds a predetermined value, with a zero value, and that the conversion means replaces the brightness value of a pixel that forms the brightness blurred image, and of which the brightness value is less than or equal to a predetermined value, so that the brightness value is replaced with a greater brightness value as the brightness value is smaller.

In the aforementioned structure, when a white portion that is larger than a predetermined size is present in an image, the light amount of illumination light is reduced by the high brightness pixel group detection means and the light amount adjustment means. However, even if a white portion is present in the image, if the size of the white portion is less than or equal to a predetermined size, the light amount of the illumination light is not adjusted. Specifically, even if halation occurs, if the degree of the halation is not one that causes a problem in diagnosis, the light amount is not excessively reduced.

Further, in the aforementioned structure, the brightness value of a pixel, of which the brightness value is less than or equal to a predetermined value, is corrected to a brightness value that is greater than or equal to the predetermined value by the conversion means. Therefore, even if a light amount in some area of the image is insufficient by reducing the light amount of the illumination light, it is possible to obtain a light easily-observable image as a whole including the insufficiently illuminated area.

BRIEF DESCRIPTION OF THE DRAWINGS

FIG. 4 is a diagram illustrating a brightness value conversion table of brightness blurred images;

FIG. 5A is a diagram for explaining a result of processing by the signal processing circuit;

FIG. 5B is a diagram for explaining a result of processing by the signal processing circuit; and FIG. 5C is a diagram for explaining a result of processing by the signal processing circuit.

DESCRIPTION OF THE PREFERRED EMBODIMENTS

Figure 1:
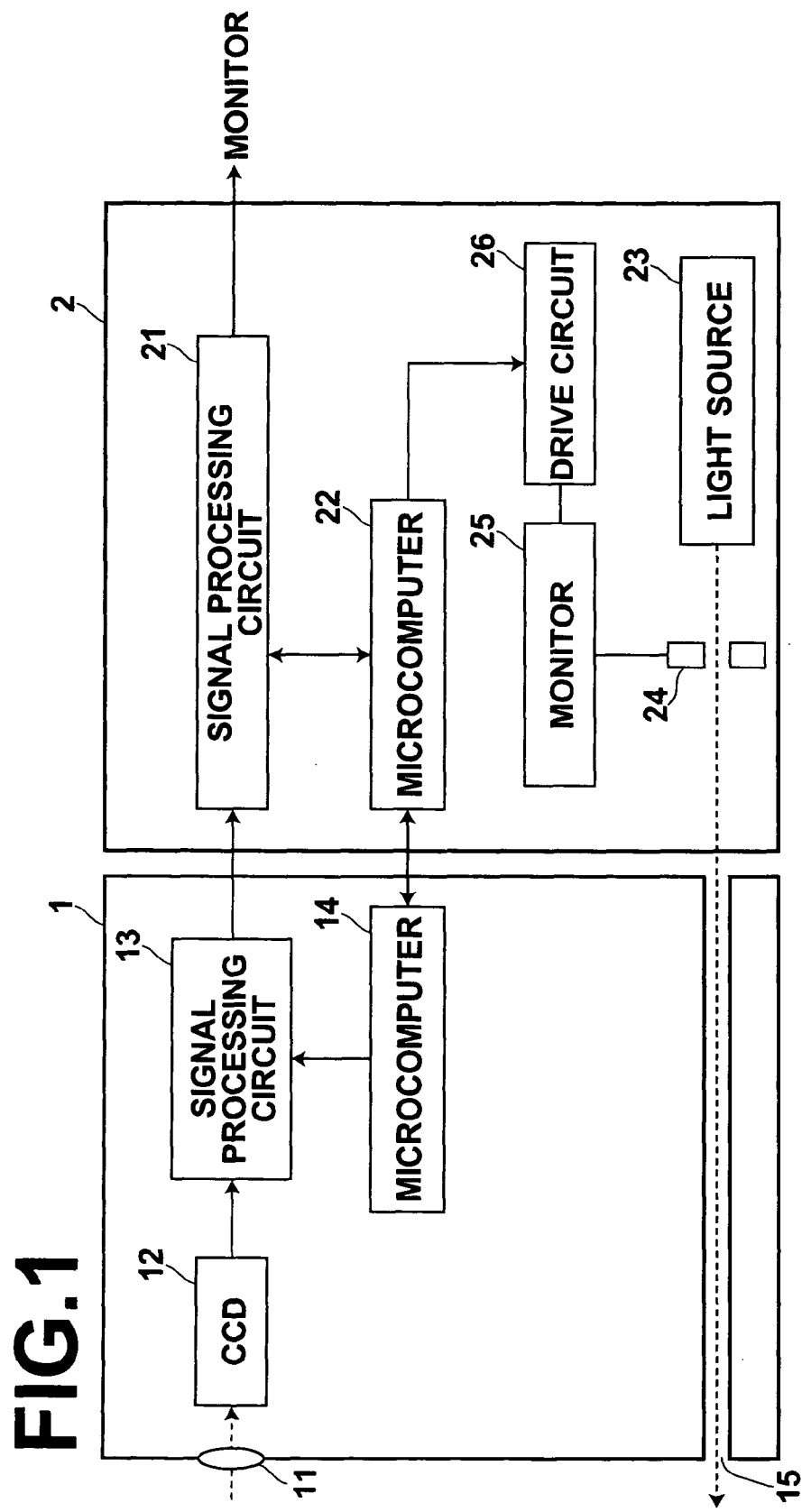
FIG. 1 is a schematic diagram illustrating the configuration of an electronic endoscopic apparatus in an embodiment of the present invention.

FIG. 1 is a schematic diagram illustrating the configuration of an electronic endoscopic apparatus in an embodiment of the present invention. The electronic endoscopic apparatus includes an electronic endoscope 1 (hereinafter, referred to as a scope 1) and a processing apparatus 2 (hereinafter, referred to as a processor 2). Further, a monitor and a printer (not illustrate) are connected to the processor 2.

The scope 1 includes an object lens 11, a CCD (charge coupled device) 12, a signal processing circuit 13 and a microcomputer 14. The signal processing circuit 13 processes signals obtained by the CCD 12, and the microcomputer 13 performs various kinds of control processing. The object lens 11 and the CCD 12 are mounted onto the leading edge of the scope 1. The CCD 12 obtains light reflected by an object to be observed, and converts the obtained reflection light into electric signals. In the present embodiment, a mosaic filter is provided for the CCD 12, and a simultaneous method is adopted. In the simultaneous method, information about each color of the object to be observed is simultaneously obtained by obtaining the reflection light from the object to be observed through the mosaic filter. However, it is not necessary that the simultaneous method is adopted. Alternatively, a monochrome CCD may be used, and a plane-sequential method may be adopted. In the plane-sequential method, while a rotary filter provided in a light emission direction of a light source (which will be described later) is rotated, light reflected from the object to be observed by illuminating the object to be observed with illumination light of each color is sequentially obtained.

The signal processing circuit 13 reads out image signals for one frame from the CCD 12 at time intervals controlled by a timing generator (not illustrate). Then, the signal processing circuit 13 performs signal processing, such as correlated double sampling, automatic gain control and A/D (analog/digital) conversion. After the image signals are processed by the signal processing circuit 13, the image signals for each frame are sent to the processor 2. The operation of the signal processing circuit 13 and data transfer to the processor 2 are controlled by the microcomputer 14. Further, the scope 1 includes a light guide 15 and a connector portion (not illustrated). The light guide 15 guides the illumination light supplied by the processor 2 to the leading edge of the scope 1, and the connector portion is connected to the processor 2.

The processor 2 includes a connector portion (not illustrated) The connector portion of the processor 2 is structures so as to be easily connected to or disconnected from the connector portion of the scope 1. Further, the processor 2 includes a signal processing circuit 21. The signal processing circuit 21 performs processing, such as gamma correction, pixel number conversion and D/A (digital/analog) conversion, on image signals input from the signal processing circuit 13 of the scope 1 through the connector portions, and generates signals to be output to the monitor. The signal processing circuit 21 performs brightness image production processing, high brightness pixel group detection processing and brightness conversion processing, which will be described later, in the process of producing the image to be output to the monitor.

Further, the processor 2 includes a light source 23, an iris (aperture diaphragm) 24 provided in a light emission direction of the light source 23, a motor 25 for opening and closing the iris 24 and a drive circuit 26 for controlling the drive of the motor 25. When light is output from the light source 23 through the iris 24, the light is guided to the leading edge of the scope 1 through the light guide 15 of the scope 1, and an object to be observed is illuminated with the light. Specifically, the light amount of the illumination light is controlled by the iris 24, the motor 25 and the drive circuit 26.

Further, the processor 2 includes a microcomputer 22 for controlling the operation of the signal processing circuit 21, communication with the scope 1 and the drive circuit 26. The microcomputer 22 judges, based on a signal supplied from the signal processing circuit 21, whether adjustment of the light amount is necessary. If adjustment is necessary, the microcomputer 22 sends an instruction signal to the drive circuit 26. Specifically, adjustment of the light amount is performed by the microcomputer 22.

Figure 2:
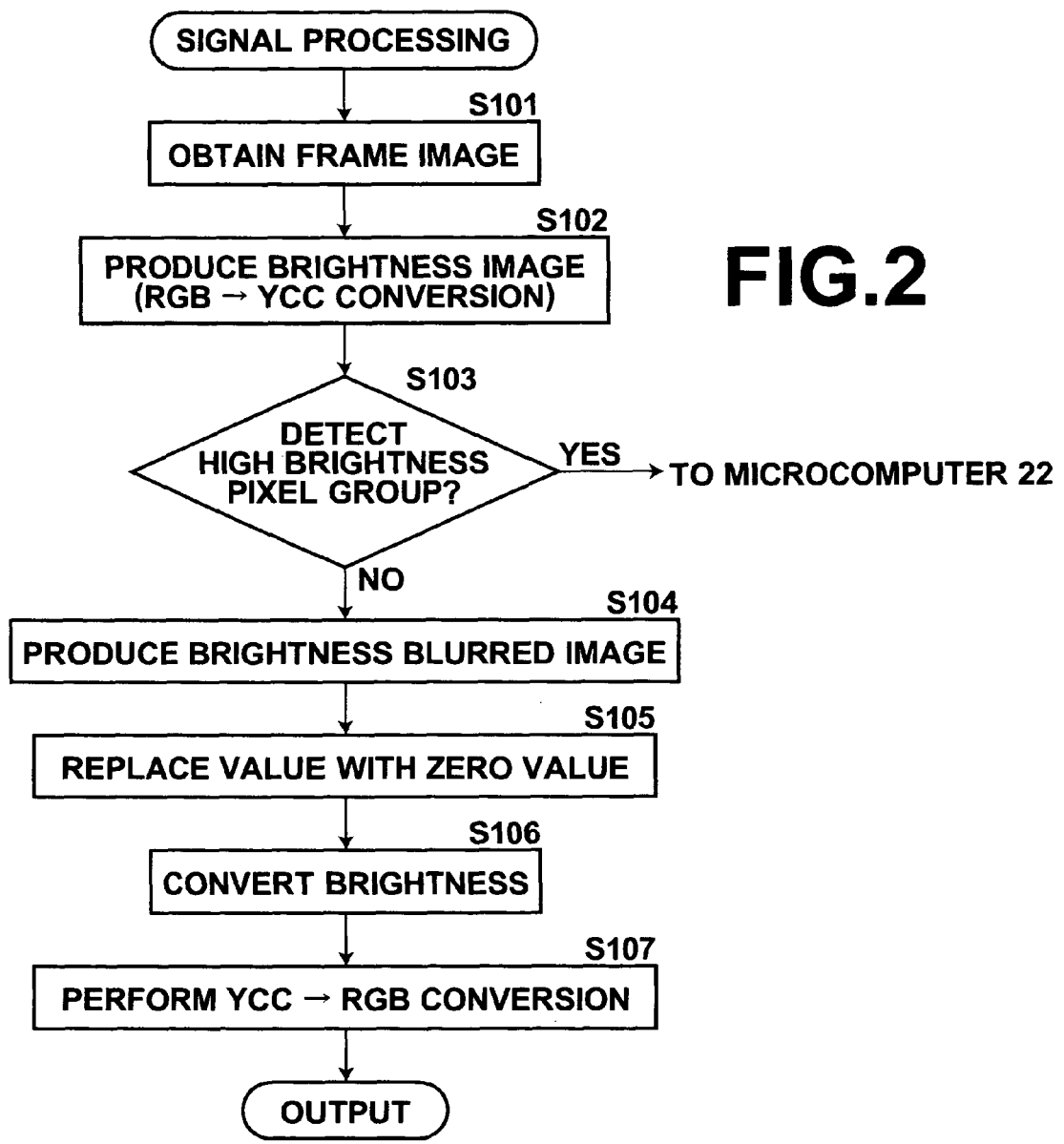
FIG. 2 is a flow chart of processing regarding lightness adjustment by a signal processing circuit.

FIG. 2 is a flow chart illustrating processing performed by the signal processing circuit 21. In FIG. 2, only processing for adjusting the lightness of an image is illustrated. When the signal processing circuit 21 obtains a frame image input from the scope 1 (step S101), the signal processing circuit 21 produces a brightness image including only a brightness component Y by performing RGB-YCC conversion on the frame image (step S102). Then, the signal processing unit 21 performs high brightness pixel group detection processing, as illustrated in FIGS. 3A and 3B, using the brightness image.

Figure 3A:
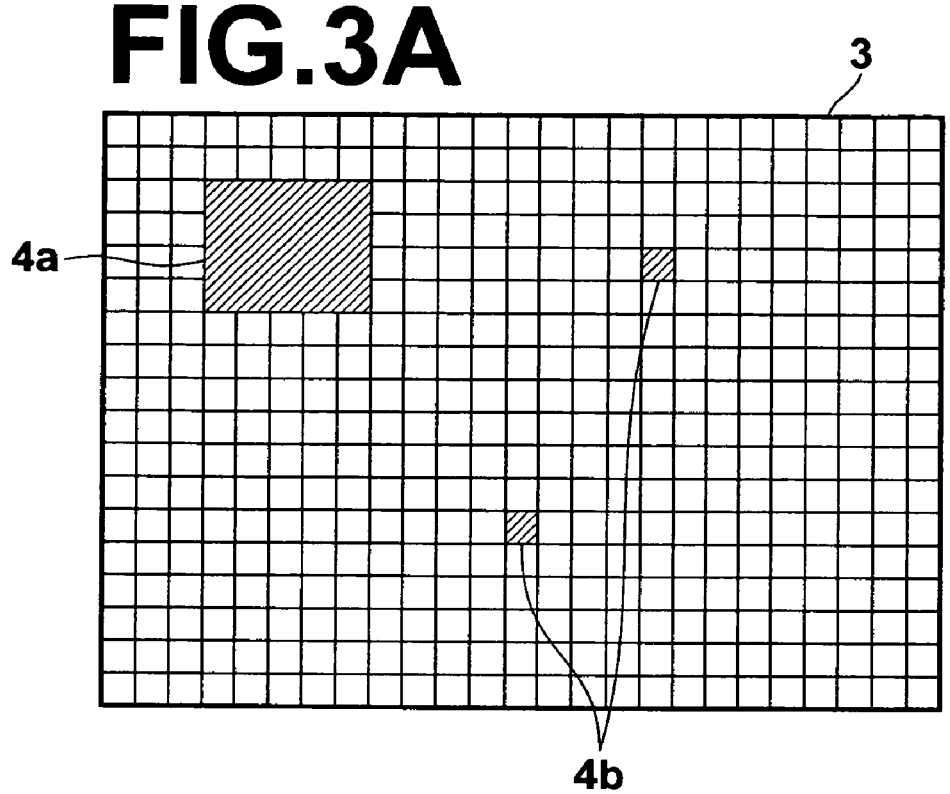
FIG. 3A is a diagram for explaining high brightness pixel group detection processing.
Figure 3B:
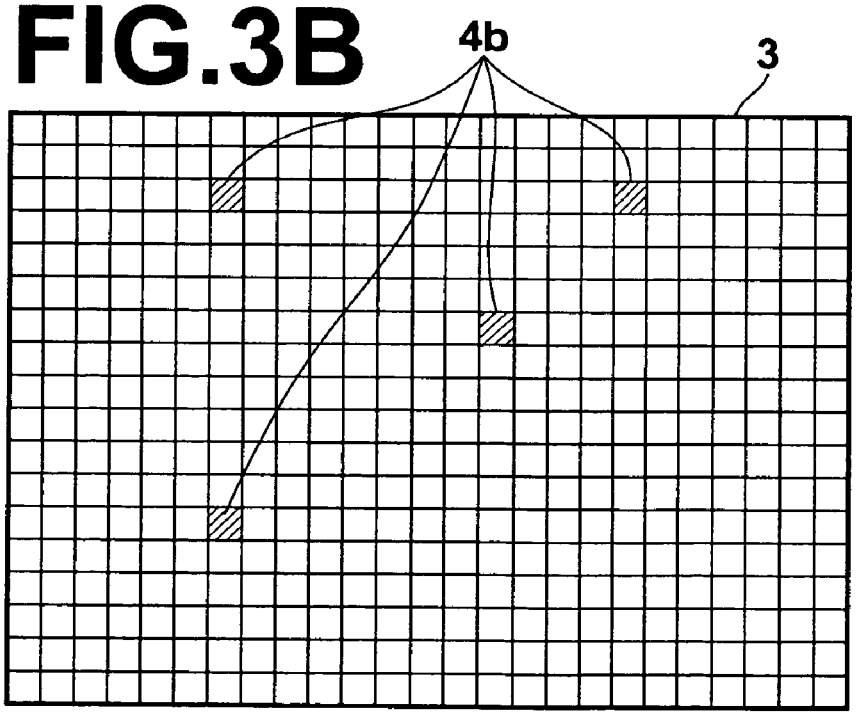
FIG. 3B is a diagram for explaining high brightness pixel group detection processing.

In FIGS. 3A and 3B, a brightness image 3 is illustrated. In FIGS. 3A and 3B, each frame separated by a grid represents a pixel forming the brightness image. A shaded pixel represents a pixel, of which the value is greater than or equal to a predetermined threshold value. In the present embodiment, the value of each pixel is represented in 8 bits. Therefore, the value is within a range of 0 to 255. In the present embodiment, the threshold value is 255, in other words, a maximum possible pixel value. However, it is needless to say that the threshold value may be set to a value other than 255.

The signal processing circuit 21 sequentially compares the value of each of pixels forming the frame image with a threshold value. When the signal processing circuit 21 detects a pixel, of which the value is greater than or equal to the threshold value (255), the signal processing circuit 21 performs threshold value judgment, based on the detected pixel, on a pixel adjust to the detected pixel in a similar manner. In a pixel group 4a illustrated in FIG. 3A, the values of more than or equal to ten pixels adjacent to each other are greater than or equal to the threshold value. When the values of more than or equal to ten pixels adjacent to each other are greater than or equal to the threshold value, the signal processing circuit 21 detects the pixel group as a high brightness pixel group. However, a condition for judging a high brightness pixel group, namely, the number of pixels forming the pixel group may be determined based on the degree of halation that should be suppressed. Therefore, it is not necessary that the number of pixels forming the pixel group is always ten.

When the image processing circuit 21 detects a high brightness pixel group, the image processing circuit 21 sends a signal for notifying detection of the high brightness pixel group to the microcomputer 22, as illustrated in step 103 in FIG. 2. Meanwhile, when a pixel, such as pixels 4b illustrated in FIGS. 3A and 3B, of which the value is greater than or equal to a threshold value, is detected, if the values of pixels in the vicinity of the detected pixel is less than the threshold value, the image signal processing circuit 21 does not notify the microcomputer 22. Further, when a pixel of which the value is greater than or equal to the threshold value is detected, even if the values of pixels in the vicinity of the detected pixel is greater than or equal to the threshold value, if the total number of pixels of which the values exceed the threshold value is less than ten, the image signal processing circuit 21 does not notify the microcomputer 22.

When the microcomputer 22 receives a signal notifying detecting of a high brightness pixel group, the microcomputer 22 compares the number of detected high brightness pixel groups with a set value (for example, 1 or a value greater than or equal to 2). If the number of the detected high brightness pixel groups exceeds the set value, the microcomputer 22 sends an instruction for lowering a light amount by a predetermined amount to the drive circuit 26, illustrated in FIG. 1. When the drive circuit 26 receives the instruction signal, the drive circuit 26 drives the motor 25 to narrow the aperture of the iris 24. Accordingly, the diameter of the light emitted from the light source 23 becomes narrower, and the intensity of light projected onto the object to be observed through the light guide 15 is lowered. In this case, a next image obtained by the signal processing circuit 21 in step S101 is an image photographed with illumination light weaker than illumination light in the previous photography. Processing in steps S102 and S103 is performed on the frame image in a manner similar to the previous processing. If a high brightness pixel group is detected again, the microcomputer 22 performs light amount adjustment again, and similar processing is repeated in step S103 until no high brightness pixel group is detected.

When it is judged that no high brightness pixel group is present in the entire area of the image in the first high brightness pixel group detection processing or as a result of peforming light amount adjustment by the microcomputer 22, the signal processing circuit 21 produces a brightness blurred image from the brightness image produced in step S102 (step S104). The brightness blurred image is an image including only a low frequency component of the brightness image. The brightness blurred image is produced by performing filtering processing on the brightness image using a low-pass filter.

Then, the signal processing circuit 21 converts the values of pixels forming the brightness blurred image using a table illustrated in FIG. 4. Specifically, the value of a pixel, of which the brightness value is greater than or equal to a predetermined brightness value, is replaced with a zero value. Further, the brightness value of a pixel, of which the brightness value is less than or equal to a predetermined brightness value, is replaced so that the brightness value is replaced with a greater brightness value as the brightness value is smaller (step S105). Then, the signal processing circuit 21 performs brightness conversion on the brightness image by adding the brightness blurred image, on which replacement processing has been performed, to the brightness image (step S106). Then, the signal processing circuit 21 replaces the brightness image with the brightness image after conversion, and performs YCC-RGB conversion to produce an RGB image (step S107). The image processing circuit 21 outputs the RGB image to the monitor.

FIGS. 5A through 5C are diagrams for explaining an advantageous effect of processing illustrated in the flow chart of FIG. 2. A relationship between the light receiving amount of each pixel of the CCD 12 and the intensity of a video signal output to the monitor when halation is generated is indicated by a solid line in FIG. 5A. Specifically, when light, of which the light amount is greater than or equal to a predetermined amount, enters the CCD 12, the value of a pixel at a position, at which the light has entered, becomes saturated at maximum value X. Here, when the pixel value is saturated, image information corresponding to the pixel is lost.

When a high brightness pixel group is detected in step S103 and the light amount of the illumination light from lighting is reduced by a light amount adjustment function of the microcomputer 22, the amount of light received by the CCD 12 is reduced. In this case, a relationship between the light receiving amount of each pixel of the CCD 12 and the intensity of video signals output to the monitor is indicated by a solid line in FIG. 5B. In the relationship illustrated in FIG. 5B, the pixel value is not saturated. Therefore, image information for the entire area of the image is maintained. However, since the light amount is reduced, a dark area becomes darker. Therefore, if a region of interest is located in the dark area, it is difficult to perform diagnosis using the image. However, if processing in steps S104 through S106 is performed, the brightness values of pixels only in the dark area are converted into higher brightness values, as indicated by a solid line in FIG. 5C. Therefore, there is no area that is too dark to observe, and it is possible to output a light image, which is appropriate for diagnosis, to the monitor.

As described above, in the electronic endoscopic apparatus of the present embodiment, when halation occurs in a wide area that may cause a problem in diagnosis, as illustrated in FIG. 3A, the signal processing circuit 21 detects the area as a high brightness pixel group. Then, the aperture of the iris 24 is adjusted by a control operation by the microcomputer 22. Accordingly, an image appropriate for diagnosis, in which halation is suppressed, can be obtained. Meanwhile, as illustrated in FIG. 3B, when the degree of halation is one that does not cause a problem in diagnosis, the microcomputer 22 does not perform light amount adjustment. Hence, it is possible to obtain a light image appropriate for diagnosis without unnecessarily reducing the light amount.

Further, even if it is necessary to reduce the light amount to suppress halation, the brightness values of pixels only in a dark area are replaced with higher brightness values by performing processing in steps S104 through S106. Therefore, even if the light amount is reduced, there is no risk that a part of the image becomes too dark to observe for diagnosis. Specifically, it is possible to always output an image that is light and appropriate for diagnosis to the monitor.

What is claimed is:
1. An electronic endoscopic apparatus comprising:
   an endoscope; and
   a processor for processing an image obtained by the electronic endoscope, wherein
      the processor includes
         a light source,
         an illumination light amount control means,
         a brightness image production means,
         a high brightness pixel group detection means,
         a light amount adjustment means and a conversion means, and wherein
            the illumination light amount control means controls the light amount of illumination light, which is emitted from the light source and guided to a leading edge of the endoscope, and wherein
            the brightness image production means produces a brightness image representing the brightness distribution of the image, and wherein the high brightness pixel group detection means detects a high brightness pixel group in the brightness image by sequentially comparing the brightness values of each pixel forming the image with a threshold value, and when a pixel having a value greater than or equal to the threshold value is detected, performing threshold value judgment, based on the detected pixel, on a pixel adjacent to the detected pixel in a similar manner, and when the values of at least a predetermined number of pixels adjacent to each other are greater than or equal to the threshold value, detecting the at least predetermined number of pixels as a high brightness pixel group, and wherein when the high brightness pixel group detection means detects a high brightness pixel group, the light amount adjustment means instructs the illumination light amount control means to reduce the light amount until the high brightness pixel group detection means does not detect any high brightness pixel group, and wherein the conversion means converts the brightness of the image so that the brightness value of a pixel that forms the brightness image, and of which the brightness value is less than or equal to a predetermined value, becomes greater than or equal to the predetermined value.

2. An electronic endoscopic apparatus, as defined in claim 1, wherein the conversion means converts the brightness of the image by producing a brightness blurred image representing a low frequency component of the brightness image, replacing the brightness value of a pixel that forms the brightness blurred image, and of which the brightness value exceeds a predetermined value, with a zero value, and adding the brightness blurred image after the replacement processing to the brightness image.

3. An electronic endoscopic apparatus, as defined in claim 2, wherein the conversion means replaces the brightness value of a pixel that forms the brightness blurred image, and of which the brightness value exceeds a predetermined value, with a zero value, and wherein the conversion means replaces the brightness value of a pixel that forms the brightness blurred image, and of which the brightness value is less than or equal to a predetermined value, so that the brightness value is replaced with a greater brightness value as the brightness value is smaller.

* * * * *